(12) United States Patent
Luecken et al.

(10) Patent No.: US 9,147,551 B2
(45) Date of Patent: Sep. 29, 2015

(54) METHOD FOR ELECTRON TOMOGRAPHY

(71) Applicant: FEI Company, Hillsboro, OR (US)

(72) Inventors: Uwe Luecken, Südbrookmerland (DE);
Remco Schoenmakers, Best (NL);
Johannes Antonius Maria van den Oetelaar, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/298,919

(22) Filed: Jun. 7, 2014

(65) Prior Publication Data

US 2015/0069231 A1    Mar. 12, 2015

(30) Foreign Application Priority Data

Jun. 6, 2013   (EP) .................................... 13170871

(51) Int. Cl.
*H01J 37/20* (2006.01)
*G01N 23/04* (2006.01)
*H01J 37/22* (2006.01)
*H01J 37/28* (2006.01)

(52) U.S. Cl.
CPC .............. *H01J 37/20* (2013.01); *G01N 23/046* (2013.01); *H01J 37/22* (2013.01); *H01J 37/28* (2013.01); *H01J 2237/20207* (2013.01); *H01J 2237/20228* (2013.01); *H01J 2237/20235* (2013.01); *H01J 2237/20264* (2013.01); *H01J 2237/20285* (2013.01); *H01J 2237/2802* (2013.01)

(58) Field of Classification Search
USPC ............................................. 250/311, 442.11
See application file for complete search history.

(56) References Cited

U.S. PATENT DOCUMENTS

| 7,884,326 | B2 | 2/2011 | van de Water et al. |
| 8,592,762 | B2 | 11/2013 | Luecken et al. |
| 8,618,478 | B2 | 12/2013 | Smit et al. |
| 8,633,456 | B2 | 1/2014 | Buijsse et al. |
| 8,912,491 | B2 | 12/2014 | Schoenmakers et al. |
| 8,938,111 | B2 | 1/2015 | Kingston et al. |
| 2009/0065708 | A1 | 3/2009 | Moon et al. |
| 2011/0284744 | A1* | 11/2011 | Zewail et al. ................. 250/307 |
| 2014/0233691 | A1 | 8/2014 | Sheppard et al. |

FOREIGN PATENT DOCUMENTS

| EP | 1970936 | 9/2008 |
| EP | 1975974 | 10/2008 |

OTHER PUBLICATIONS

Baumeister, Wolfgang, et al., "Electron tomography of molecules and cells," Trends in Cell Biology, Feb. 1999, pp. 81-85, vol. 9, No. 2.

(Continued)

*Primary Examiner* — Kiet T Nguyen
(74) *Attorney, Agent, or Firm* — Scheinberg & Associates, PC; Michael O. Scheinberg

(57) ABSTRACT

The invention relates to an improved method of electron tomography. Electron tomography is a time consuming process, as a large number of images, typically between 50-100 images, must be acquired to form one tomogram. The invention teaches a method to shorten the time needed to acquire this amount images much more quickly by tilting the sample continuously, instead of step-by-step. Hereby the time needed to reduce vibrations between steps is eliminated.

20 Claims, 3 Drawing Sheets

(56) References Cited

OTHER PUBLICATIONS

Figure 1:
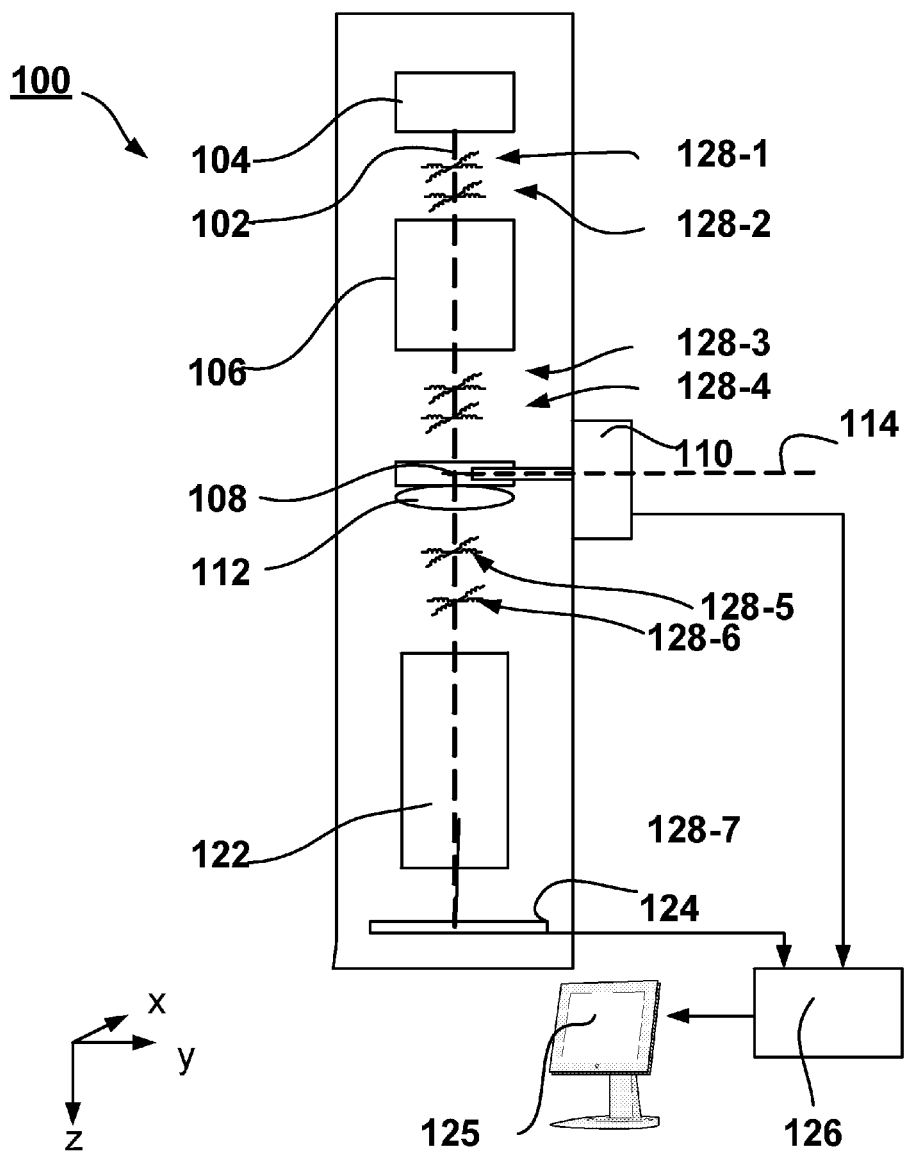

Unknown, "Functional description of Tecnai Tomography Software," FEI Company Technical Note, Dec. 2003, pp. 1-20.

Moret, J., et al, "3D Rotational Angiography: Clinical Value in Endovascular Treatment", MedicaMundi, vol. 42, Issue 3, Nov. 1998.

* cited by examiner

METHOD FOR ELECTRON TOMOGRAPHY

The invention relates to a method of performing electron tomography on a sample, said sample mounted on a sample holder in a electron microscope, the electron microscope comprising an electron source for generating a beam of energetic electrons along an optical axis and optical elements for focusing and deflecting the beam so as to irradiate the sample with a beam of electrons, the sample holder capable of orienting and tilting the sample with respect to the electron beam, the method comprising acquiring a tilt series of images by irradiating the sample with the beam of electrons, each image acquired at an associated unique tilt angle, the images recorded on a camera with a read-out speed Such a method is inter alia known from "Technical note: Functional description of Tecnai™ Tomography Software" FEI Company, version 31 December 2003.

In an electron microscope, such as a Transmission Electron Microscope (TEM) an electron source produces a beam of energetic electrons with a selectable energy of, for example, between 80-300 keV, although higher and lower energies are known to be used. This beam is manipulated (focused, deflected) by optical elements (electron lenses, deflectors, multipoles) and irradiates a sample placed in a sample holder. The sample holder positions the sample, the holder typically showing three translational degrees of freedom (x, y, z) and one rotational degree of freedom ($\alpha$) or more rotational degrees of freedom. The sample is sufficiently thin to be transparent to electrons: some electrons are absorbed, but many electrons pass the sample while being scattered or unscattered. Typically the thickness of the sample is between 50 nm and 1 μm for biological samples (50-200 nm for cryogenic samples), and less than 100 nm for semiconductor samples. Another set of optical elements form an enlarged image of the sample on a detector, such as a CMOS camera, a CCD camera, a fluorescent screen, or a combination of fluorescent screen and camera connected via fiber optics.

As described in the Technical Note, the image formed on the detector is a 2D projection of the sample. To achieve a 3D image, a series of images of the sample under different rotational orientations is acquired in a so-called tilt-series. Typically the tilt series covers a tilt range from −70 to +70 degrees with regular intervals of 1 or 2 degrees. The images of the tilt series are then aligned with respect to each other, and a 3D reconstruction is made using appropriate software, after which visualization may take place.

For each of the images of the tilt series the sample must be oriented to another tilt angle. Due to the high resolution of a TEM, the sample should be stabilized to within, for example, 1 nm or less. Therefore typically a relaxation time of 1 second or more is used to damp the vibrations. As a result of this the acquisition of a tilt series is a time consuming process.

There is a need for a quicker method of acquiring the tilt series.

To that end the method according to the invention is characterized in that the sample holder is changing the tilt angle continuously while acquiring the tilt series and the position of the sample is changed continuously to keep the sample on the optical axis.

Until now there is a strong prejudice that "tomo-on-the-fly", that is tomography where the tilt series is acquired while the tilt angle is continuously changed, does not work due to vibrations etc. with each acquisition. In other words: electron microscopists were used to stop any movement of the sample before acquiring a high resolution image. Inventors realized that two separate developments make tomo-on-the-fly possible: a fast acquisition time and a smooth tilt mechanism.

Fast acquisition time: until recently the acquisition time of the camera's used in electron microscopy, camera's combining low noise, high sensitivity and high dynamic range at 2048×2048 pixels was typically in the order of 1 second or more. Recent developments in CMOS technology enable a read-out speed of 20 frames per second or more. A tilt series of 100 images can thus be acquired in a few seconds.

Smooth tilt mechanism: a smooth tilt mechanism is necessary so that no or little vibration due to rotational acceleration occurs. Such a tilt mechanism is described in e.g. U.S. Pat. No. 7,884,326 B2. This patent describes how a sample carrier is connected with a spindle in the plane of the sample. By now rolling this spindle between actuators, a rotation occurs. As this is achieved by rolling the spindle over actuators actuated by piezo-elements, a smooth movement is achieved.

Inventors concluded that the prejudices no longer hold.

It is noted that the area-of-interest is often not on the rotation axis, making it necessary to simultaneously translate the sample smoothly without introducing vibrations. It is known to achieve this using piezo-actuators.

The advantages of the method according to the invention are that no time is lost for stabilizing the (rotational) position of the sample holder, and that the camera is acquiring images continuously. Related to that all electrons used to irradiate the sample and impinging on the camera are used in imaging, and thus no useless sample deterioration occurs.

It is noted that a sample, especially a biological sample, deteriorates due to radiation damage resulting from electron irradiation.

It is noted that in prior art methods the rotational mechanism of the sample stage used for taking a tilt series is typically placed between the "world" and the relatively heavy sample rod on which the sample is mounted. This results in a relative low eigen frequency and thus long time needed for these vibrations to damp out. Also the way in which the rotation is realized results in vibrational amplitude much larger than one pixel, thus deteriorating the quality of the image. In the prior art methods thus time is lost for stabilizing the sample holder (to allow for damping of vibrations).

It is noted that for prior art electron tomography repositioning of the sample is needed for each image, as the volume-of-interest is typically removed from the tilt axis. When using the method according the invention this implies a continuous repositioning. The repositioning is typically a repositioning perpendicular to the tilt axis and a repositioning along the optical axis, although the latter may also be realized by re-focusing.

In an embodiment of the invention the images of the sample are imaged on a pixilated camera, and the velocity of the tilt angle, expressed in degrees per second, and the read-out speed of the camera, expressed in frames per second, are matched so that the displacement of the image due to the tilt change during one frame is less than one pixel, more specifically less than half a pixel.

By so matching the tilt speed and the read-out speed, the resolution of the camera is optimally used. Known camera's for these purposes comprise, for example, 4096*4096 pixels. The read-out speed of the camera can be limited by the possibilities of the camera, or by the need for a sufficient number of electrons in one image. It is noted that it is possible to integrate many images, each with a low number of electrons, but compared to one image with a longer illumination time and an identical number of detected electrons as available in the integrated set of images this results in a lower signal-to-noise ratio. Therefore the acquisition of one image with a longer frame time is preferred over the integration of several images with a lower frame time. This may thus lead to the choice of a read-out speed of the camera and the tilt speed of the sample holder, in which each frame comprises sufficient electrons, both for the number of electrons needed for forming a 3D reconstruction (a tomogram) and for acquiring the data needed for shifting the images with respect to each other (using, for example, correlation techniques).

In another embodiment of the invention the velocity of the tilt is modulated.

The rotation of the sample results in a change of the image. This change is a function of the tilt angle: $\Delta = d \cdot \sin \alpha$, with $\Delta$ the displacement of an image point due to the rotation, d the distance of the point of the sample with respect to the tilt axis and $\alpha$ the tilt axis. For an identical displacement between images, at small tilt angles (sample perpendicular to the optical axis), the tilt speed can thus be larger than for high tilt angles.

In another embodiment of the invention a shift and/or rotational correction of the images forming the tilt series is applied relative to each other.

The images forming the tilt series should be arranged shifted and rotated such that one point on the tilt axis is taken as reference for all images.

In a further embodiment this includes a pair-wise correction. However, if the images comprise too little information per image for the algorithm used, an algorithm using two or more sets of images may be used, where, for example, the shift and/or rotational correction is based on the information of two sets comprising two images each.

In a further embodiment the sample comprises markers.

By using markers, such as gold markers with a diameter of, for example, 10 to 20 nm, the position and orientation of each of the images is more easily found. Preferable more than one marker is used to enable not only shift correction, but also rotational correction of the images forming the tilt series. Also the tilt angle may be derived from the relative position of a set of markers.

In another embodiment of the invention the excitations of the lenses of the microscope are not changed during the acquisition of the tilt series.

The lenses in an electron microscope are typically magnetic lenses. Changing the excitation of such a lens results in thermal drift, hysteresis, etc. By keeping the excitation constant these effects are kept to a minimum.

Preferably also the excitation of other optical elements, such as deflectors, stigmators and correctors, are kept constant as well.

It is noted that the invention superficially resembles the tomography method as used by CT-tomography and as described in, for example, "3D rotational angiography: Clinical value in endovascular treatment", J. Moret et al., Medica-Mundi, Vol. 42 Issue 3 (November 1998). However, there are some important differences:

In CT-tomography X-rays are used to irradiate the sample (patient).

In CT-tomography the mechanical construction of the so-called C-arm, on which X-ray source and X-ray detector are mounted, is rotated round the sample (patient).

In CT-tomography the images are not aligned, but the so-called C-arm is calibrated to compensate for distortion such as resulting from the earth's magnetic field. In an electron microscope the orientation of the optical axis is kept constant and the sample is rotated as otherwise the optical alignment would be completely lost, both due to mechanical changed and changes in environmental magnetic fields. Also, the volume-of-interest is always projected on the detector in all images of the tilt series, due to the C-arm rotating round this volume-of-interest, the intersect at the volume-of-interest typically being much larger than the volume-of-interest and the sample (patient) being much larger (thicker) than the volume-of-interest, The C-arm is easily made rigid enough to show vibrations corresponding to much less than a pixel/voxel, as a voxel typically is in the order of $1 \times 0.8 \times 0.7$ mm$^3$ or more, allowing vibrations and mechanical uncertainties in the order of 0.4 mm, whereas a voxel in an electron tomogram typically is in the order of $10 \times 10 \times 10$ nm$^3$ to less than $1 \times 1 \times 1$ nm$^3$, demanding vibrations and mechanical uncertainties in the order of 0.5 nm or less.

The C-arm only shows rotation, detector/source are not shifted with respect to the sample (patient). In electron tomography this is typically done to keep the volume-of-interest on the optical axis.

It is noted that Magnetic Resonance Imaging (MRI) also differs from the invention in that the sample/patient is irradiated with RF magnetic fields, the sample is not rotated with respect to the source/detector (the electric coils), but only a stepwise shift is applied to the sample (patient), and the voxel size is approximately $0.5 \times 0.5 \times 0.5$ mm$^3$. Therefore sufficient time is available for the moving object (patient) to come to rest after a displacement.

The invention is now elucidated using figures, in which identical numerals refer to corresponding features.

To that end:

FIG. 1 schematically depicts a transmission electron microscope.

Figure 2A:
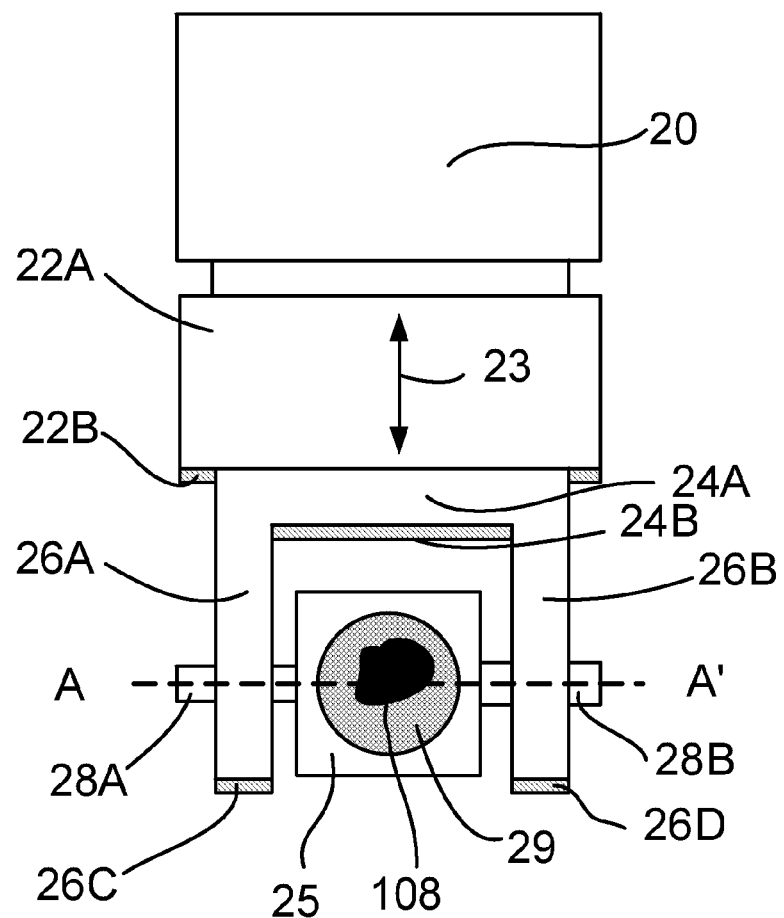

FIG. 2A schematically depicts a tilt motor enabling smooth tilting, and

Figure 2B:
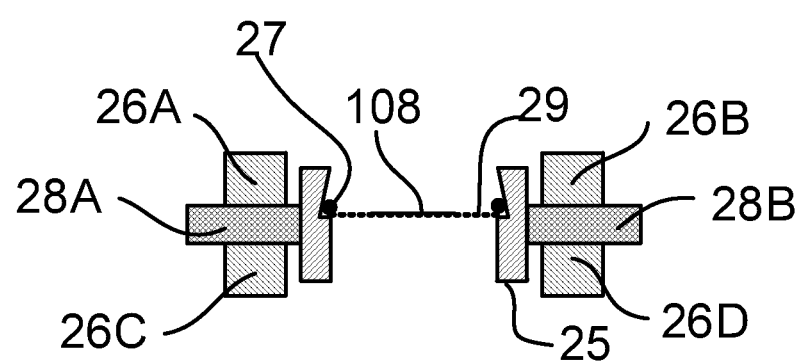

FIG. 2B shows a typical workflow used to make a tomogram.

FIG. 1 schematically shows a TEM 100. A particle source 104 produces a beam of electrons along optical axis 102. The electrons have a selectable energy of typically between 80-300 keV, although higher energies, e.g. 400 keV-1 MeV, or lower energies, e.g. 50 keV, may be used. The beam of electrons is manipulated by condenser system 106 to form a parallel beam impinging on a sample 108, the sample positioned with a sample holder 110. The sample holder can position the sample with respect to the optical axis and may shift the sample in the plane perpendicular to the optical axis and tilt the sample with respect to a tilt axis 114 perpendicular to the optical axis. Objective lens 112 forms a magnified image of the sample. A projection system 122 forms a magnified image of the sample on a pixilated detector 124, thereby revealing sample details of e.g. 0.1 nm. The detector may take the form of, for example, a CCD or CMOS camera. To align the optical components on the axis the TEM comprises a large number of deflectors, schematically shown as 128-1 . . . 128-6, although other deflectors on other places may be included. Sample holder 110 and camera system 124 are controlled by a controller 126, the controller equipped to convert the tilt series to a 3D tomogram and to visualize the tomogram on a screen 125. It is noted that for visualization specialized software is used, such as described in earlier mentioned technical note: "Functional description of Tecnai™ Tomography Software".

To perform the method according to the invention on the electron microscope depicted in this figure, the controller 126 must be programmed to store in a memory the image acquired via camera system 124 while controlling the sample holder 110 to tilt with a controlled tilt velocity round tilt axis 114. Furthermore the sample stage should be able to tilt the sample over a large angle (typically −80 to +80 degrees) in order to get sufficient data to reconstruct a 3D image of the sample. The controller should also be able to control the position of the sample with respect to the optical axis in order to keep the volume-of-interest on the optical axis. This is done by either controlling deflectors, for example deflectors 128-3 ... 128-5, or by mechanically moving the sample with respect to the stationary optical axis by controlling the sample holder 110 accordingly.

While acquiring images for the tilt series the position of the sample must be corrected so that the volume of interest stays in view and in focus. This typically demands positioning within 1 μm along the optical axis (to stay in focus) and perpendicular to the optical axis a vibration level within a camera frame time of less than a pixel (projected back to the sample), typically less than 1 nm. It is noted that deviations of the position between frames is corrected for by aligning the images forming the tilt series, as long as the volume-of-interest is kept in view. Sample holders capable of such x/y/z positioning are known, typically using piezo-actuators to achieve the required stiffness, speed and accuracy. The combination with a large angle tilt motor for smoothly rotating the sample around the tilt axis, as described in e.g. U.S. Pat. No. 7,884,326 B2, enables the invention.

FIG. 2A shows a tilt manipulator in which a sample holder with two protruding axles is clamped between two pair driving surfaces, as described in U.S. Pat. No. 7,884,326 B2. FIG. 2A shows a base 20, preferably mounted on an actuator capable of x/y/z translational positioning. On the base two actuators 22A, 22B, for example piezo-actuators, are mounted. The actuators can be shortened/lengthened in direction 21. Actuator 22B, shown hatched, is in this figure slightly longer than actuator 22A. To each actuator 22A, 22B a member is connected. Member 24A is connected to actuator 22A and member 24B (shown hatched) is connected to actuator 22B. Member 24A has two extremities, 26A and 26B, and member 24B has two extremities 26C and 26D (shown hatched).

The sample holder shows two axles, 28A and 28B, arranged along a common axis, the tilt axis. A block 25 is mounted on the axles, and a standard microscope grid 29 is mounted in the block for holding the sample 108.

Axle 28A of the sample holder is clasped between extremities 25A and 26C, while axle 28B of the sample holder is clasped between the extremities 26B and 26D.

The tilt axis coincides with the centre of the axles, and thus coincides with line AA'.

FIG. 2B shows a cross-section along line AA', the tilt axis. It shows the extremities 26A and 26C between which axle 28A is clasped, and extremities 26B and 26D between which axle 28B is clasped. By rotating the axles the block 25, the grid inserted in the block and the sample mounted on the grid are rotated round the tilt axis. As shown grid 29 is held in place by a circular spring 27.

By moving actuator 22A in one direction and actuator 22B in the other direction over an equal length (with respect to the base 20), extremities 26A and 26B will move in one direction with respect to the sample holder and extremities 26C and 26D in the opposite direction. A rotation of axles 28A and 28B with respect to the base results, and thus a rotation of the sample holder round the tilt axis.

FIG. 2B shows a typical workflow used to make a tomogram.

In a step 301 a sample is placed in a TEM.
In step 302 the volume-of-interest is located. This may involve the location of markers, etc.

In step 303 the TEM is optimally focused on the volume of interest. Defocus is set to obtain an optimum between contrast and resolution.
In step 304 the sample is rotated to its first (extreme) tilt angle of, for example, −70 degrees.
The sample is then ready for the tilt series.
In step 305 the tilt series is started and the tilt is gradually but continuously changed to its other extreme tilt angle, for example +70 degrees.
In step 306, while performing step 305, the volume-of-interest is kept in view and in (de)focus by x/y/z translation.
In step 307, when all images forming the tilt series are acquired, the images forming the tilt series are aligned. It is noted that this may already start while the images are acquired. Also, the outcome of this step may be used for the movement of step 306.
In step 308 the tilt series is used for computing a tomogram. It is noted that this step can already start while information is still acquired, thus shortening the total time needed.
In step 309 the tomogram is visualized based on user input (demanded slice plane, angle, thickness, contrast, etc).

As is clear to the skilled person, this is only one of many implementations of the workflow. For example, the workflow can be modified, or other steps can be added.

To show the feasibility of this scheme and the obtainable shortening of process time, the following exemplary calculations are made:

Using a constant tilt speed, the maximum speed is dictated by the displacement of 0.5 pixel at the extreme tilt range during one frame exposure (one image acquisition).
At a tilt angle α of 70 degrees, the maximum allowable difference in tilt angle between two acquisitions, Δα, is thus the Δα for which $$\cos\alpha - \cos(\alpha - \Delta\alpha) = 0.5/(N/2),$$

with N the number of pixels. It is noted that N/2 is used due as sampling should be done with a frequency lower than the Nyquist frequency.

Assuming a CMOS camera with N=4096, the tilt difference Δα is 0.03 degrees.
Assuming a frame rate of 40 images per second, the tilt speed is thus 40×0.03 degrees/second=1.2 degrees per second.
A full tilt series from −70 degrees to +70 degrees can be acquired in 140 degrees/(1.2 degrees/second), less than two minutes.

This is in contrast with prior art electron tomography, which typically uses in the order of one hour for the acquisition of 100 images.

Non-patent Literature

[-1-] Technical note: "Functional description of Tecnai™ Tomography Software", FEI Company, version 31 Dec. 2003.
[-2-] "3D rotational angiography: Clinical value in endovascular treatment", J. Moret et al., MedicaMundi, Vol. 42 Issue 3 (November 1998).

The invention claimed is:
1. A method of performing electron tomography on a sample, said sample mounted on a sample holder in an electron microscope, the electron microscope comprising an electron source for generating a beam of energetic electrons along an optical axis and optical elements for focusing and deflecting the beam so as to irradiate the sample with a beam of electrons, the sample holder capable of orienting and tilting the sample with respect to the electron beam, the method comprising:

acquiring a tilt series of images by irradiating the sample with the beam of electrons, each image acquired at an associated unique tilt angle, the images recorded on a camera with a read-out speed, wherein:

the tilt angle is changed continuously while acquiring the tilt series of images, and a position of the sample is changed continuously to keep the sample on the optical axis.

2. The method of claim 1, wherein the sample is imaged on a pixilated camera, and a velocity of the tilt angle, expressed in degrees per second, and the read-out speed of the camera, expressed in frames per second, are matched so that a displacement of the image due to a tilt change during one frame is less than one pixel.

3. The method of claim 2, wherein the velocity of the tilt is modulated.

4. The method of claim 1, wherein a shift and/or rotational correction of the images forming the tilt series is applied relative to each other.

5. The method of claim 4, wherein the shift and/or rotational correction is based on an algorithm using data from more than two images for correction of a relative position of multiple images simultaneously.

6. The method of claim 4 wherein the shift and/or rotational correction includes a pair-wise correction based on an algorithm using data of two images.

7. The method of claim 4, wherein the shift and/or rotational correction is based on a position of one or more markers in the image.

8. The method of claim 1, wherein excitations of focusing optical elements are not changed during acquisition of the tilt series of images.

9. The method of claim 1, wherein during acquisition of the tilt series of images excitations of the focusing optical elements are not changed and the position of the sample is continuously changed by mechanically moving the sample with respect to the optical axis.

10. The method of claim 1, wherein a focus position is changed to keep an area of interest in-position and/or in-focus while changing the tilt angle continuously.

11. The method of claim 1, wherein the electron microscope is a transmission electron microscope equipped with a programmable controller configured to control the sample holder and the camera, wherein the transmission electron microscope is programmed with software, and wherein the software enables the transmission electron microscope to perform the method of performing electron tomography on a sample.

12. A transmission electron microscope equipped for performing electron tomography, the transmission electron microscope comprising:

an electron source configured to produce a beam of electrons along an optical axis of the transmission electron microscope;

a sample holder;

a camera system for acquiring images;

a programmable controller configured to control the sample holder and the camera system; and wherein the programmable controller is programmed to control the sample holder and the camera system such that the camera can acquire a tilt series of images of a sample on the sample holder while the sample holder is tilted continuously.

13. The transmission electron microscope of claim 12, wherein the programmable controller is configured convert the tilt series of images to a 3-D tomogram.

14. The transmission electron microscope of claim 12, further comprising a memory and wherein the controller is programmed to store in the memory the images acquired by the camera system while controlling the tilting of the sample holder.

15. The transmission electron microscope of claim 12, wherein the sample holder is capable of tilting the sample over an angle of −80 degrees to 80 degrees.

16. The transmission electron microscope of claim 12, wherein the transmission electron microscope is configured to maintain the sample on the optical axis while the sample holder is tilted continuously by continuously changing a position of the sample.

17. The transmission electron microscope of claim 12, wherein the programmable controller is configured to control a position of the sample with respect to the optical axis such that a volume-of-interest of the sample is maintained on the optical axis.

18. The transmission electron microscope of claim 17, further comprising deflectors, wherein the programmable controller is configured to control the position of a sample by controlling the deflectors.

19. The transmission electron microscope of claim 12, wherein the sample holder is configured to shift the sample in a plane perpendicular to the optical axis and tilt the sample with respect to a tilt axis perpendicular to the optical axis.

20. The transmission electron microscope of claim 19, wherein the sample holder is mounted on a piezoelectric actuator capable of x/y/z translational positioning.

* * * * *